(12) United States Patent
Blalock

(10) Patent No.: US 6,897,070 B2
(45) Date of Patent: May 24, 2005

(54) DETECTION OF GAS PHASE MATERIALS

(75) Inventor: Guy T. Blalock, Boise, ID (US)

(73) Assignee: Micron Technology, Inc., Boise, ID (US)

(*) Notice: Subject to any disclaimer, the term of this patent is extended or adjusted under 35 U.S.C. 154(b) by 0 days.

(21) Appl. No.: 09/388,286

(22) Filed: Sep. 1, 1999

(65) Prior Publication Data

US 2003/0138958 A1 Jul. 24, 2003

(51) Int. Cl.$^7$ ................. G01N 33/20; G01N 27/04; C23C 16/06
(52) U.S. Cl. ................. 436/73; 118/712; 118/715; 422/88; 422/90; 422/98; 436/36; 436/76; 436/82; 436/84; 436/149; 436/182
(58) Field of Search ................. 436/36, 73, 76, 436/82, 84, 149, 151, 182; 422/88, 90, 98; 118/712, 715

(56) References Cited

U.S. PATENT DOCUMENTS

| | | | |
|---|---|---|---|
| 3,585,073 A | | 6/1971 | Veenstra |
| 3,714,562 A | | 1/1973 | McNemey |
| 3,890,703 A | | 6/1975 | Frazee et al. |
| 4,433,320 A | | 2/1984 | Murata et al. |
| 4,442,422 A | * | 4/1984 | Murata et al. ............... 338/35 |
| 4,677,416 A | | 6/1987 | Nishimoto et al. |
| 4,911,892 A | * | 3/1990 | Grace et al. ............... 422/94 |
| 5,147,737 A | | 9/1992 | Post et al. |
| 5,331,287 A | * | 7/1994 | Yamagishi et al. ......... 324/724 |
| 5,337,018 A | * | 8/1994 | Yamagishi ............... 324/693 |
| 5,653,807 A | * | 8/1997 | Crumbaker ............... 118/715 |
| 5,756,879 A | * | 5/1998 | Yamagishi et al. ......... 73/28.01 |
| 5,857,250 A | | 1/1999 | Riley et al. |
| 5,906,726 A | | 5/1999 | Schneider et al. |
| 6,280,604 B1 | | 8/2001 | Allen et al. |
| 6,436,246 B1 | * | 8/2002 | Sandhu ............... 204/192.13 |
| 6,479,297 B1 | * | 11/2002 | Sandhu ............... 436/151 |
| 6,689,321 B2 | | 2/2004 | Sandhu |
| 2004/0157340 A1 | | 8/2004 | Sandhu |

FOREIGN PATENT DOCUMENTS

| | | |
|---|---|---|
| EP | 386660 | * 12/1990 |
| FR | 1576658 | * 8/1969 |
| GB | 1151482 | * 5/1969 |
| GB | 2 048 471 | 12/1980 |
| JP | 60-210752 | * 10/1985 |
| JP | 2-69658 | * 3/1990 |
| JP | 2-293644 | * 12/1990 |
| JP | 3-48748 | * 3/1991 |

OTHER PUBLICATIONS

M. B. Bardin et al, J. Anal. Chem. (USSR) 1975.*
H. Miyashita Aneruba Giho 1996, 2, 67–71.*
J. R. Bates et al, Thin Solid Films 1997, 299, 18–24.*
H. Takayama et al; Solid State Ionics 1989, 35, 411–415.*
V. Tvarozek et al, Sens. Actuators B 1994, 18–19, 597–602.*
Y. Koda et al, Chem. Abstr. 1979, 90, abstract 114382q.*
N. N. Morgunov et al, Chem. Abstr. 1982, 96, abstract 105113z.*

(Continued)

Primary Examiner—Arlen Soderquist
(74) Attorney, Agent, or Firm—Mueting, Raasch & Gebhardt, P.A.

(57) ABSTRACT

Sensors and methods of monitoring for the presence of gas phase materials by detecting the formation of films based on the gas phase material are disclosed. Advantageously, some gas phase materials preferentially deposit on specific surfaces. As a result, selective detection of those gas phase materials can be obtained by detecting films deposited on those detection surfaces. Examples of gas phase materials that may be detected include $RuO_4$, $IrO_4$ and $RhO_4$.

24 Claims, 3 Drawing Sheets

OTHER PUBLICATIONS

J. S. Trent et al, Macromolecules 1983, 16, 589–598.*
A. P. Tyutnev et al, Phys. Status Solidii A 1984, 86, 709–716.*
H. Sano et al, Polymer 1986, 27, 1497–1504.*
K. Watari et al, Chem. Abstr. 1987, 106, abstract 91861c.*
I. S. Kolesov et al, Chem. Abstr. 1989, 110, abstract 213848j.*
B. Ohlsson et al, J. Appl. Polym. Sci. 1990, 41, 1189–1196.*
Z. uan et al, Chem. Mater. 1993, 5, 908–910.*
S. Setz et al, J. Appl. Polym. Sci. 1996, 59, 1117–1128.*
G. M. Brown et al, Polymer 1997, 38, 3937–3945.*
J. X. Li et al, J. Appl. Polym. Sci. 1999, 72, 1529–1538.*
N. A. Orlow Chem.–Ztg. 1908, 32, 77.*
A. G. Aizenshtein et al, Chem. Abstr. 1966, 64, abstract 1747.*
J. L. Provo J. Vac. Sci. Technol. 1975, 12, 946–952.*
Y. Koda et al, Kyoto Daigaku Genshiro Jikkenso Gakujitsu Koenkai Koen Yoshisu 1976, 10, 25–27.*
K. Watari et al, Nihon Genshiryoku Gakkaishi 1986, 28, 493–500.*
M. El Shabasy et al, Journal of Materials Science 1990, 25, 585–588.*
R. S. Schepis et al, Thin Solid Films 1994, 251, 99–102.*
F. Tardif et al, Chem. Abstr. 1995, 123, abstract 328462y.*
Aizenshtein, A. G. et al, Tsvetn. Metal. 1965, 38, 65–6.*
Akinfieva, T. A. Gigiena Truda i Professional'nye Zabolevaniya 1981, 46–47.*
Gale, R. P. et al, AIP Conference Proceedings 1988, 166, 145–151.*
Crawford, W. W. et al, Journal de Physique IV: Proceedings 1991, 1(C2, Proc. Eur. Conf. Chem. Vap. Deposition, 8th, 1991), C2/459–C2/466.*
Lu, P. et al, Thin Solid Films 1999, 340, 140–144.*
Kawahara et al., "(Ba, Sr)$TiO_3$ Films Prepared by Liquid Source Chemical Vapor Deposition on Ru Electrodes," *Jpn. J. Appl. Phys.*, 35, Part 1, No. 9B, pp. 4880–4885 (Sep. 1996).

* cited by examiner

DETECTION OF GAS PHASE MATERIALS

FIELD OF THE INVENTION

The present invention relates to the detection of selected materials. More particularly, the present invention pertains to the detection of gas phase materials.

BACKGROUND OF THE INVENTION

In the fabrication of integrated circuits, various layers of the same or different materials are used. For example, during the formation of semiconductor devices, such as dynamic random access memories (DRAMs), static random access memories (SRAMs), ferroelectric (FE) memories, etc., a variety of conductive and non-conductive materials are used in the formation of storage cell capacitors and also may be used in interconnection structures, e.g., conductive layers of contact holes, vias, etc.

These materials are typically supplied in a gas phase conducive to the formation of a film on a surface. When supplied in the gas phase, many of these materials may become toxic or otherwise harmful to health. As a result, it may be important to monitor where these materials are found and the concentrations in which they are found. Furthermore, because the effects may be cumulative, i.e., repeated exposure to low levels of the selected materials may be additive, it may be important to provide sensors and detection methods that are capable of measuring for cumulative exposure levels in addition to real-time exposure.

Semiconductor device manufacturing is one example of an environment in which the monitoring of exposure to potentially harmful materials can be advantageous. For example, various metals, metallic compounds, metal oxides, etc. are used to manufacture various structures used in semiconductor devices. A number of these materials may pose health risks based on exposure to the materials in the gas phase.

For example, ruthenium oxide and ruthenium have recently been employed in semiconductor devices because these materials are electrically conductive, conducive to conformal deposition, and they are easily etched. For example, the article entitled, "(Ba,Sr)TiO$_3$ Films Prepared by Liquid Source Chemical Vapor Deposition on Ru Electrodes," by Kawahara et al., *Jpn. J. Appl. Phys.*, Vol. 35 (1996), Part 1, No. 9B (September 1996), pp. 4880–4885, describes the use of ruthenium and ruthenium oxide for forming electrodes in conjunction with high dielectric constant materials. It is, however, known that gaseous ruthenium tetraoxide (RuO$_4$) is toxic at very low levels, e.g., about 1 part per billion (ppb). Monitoring of exposure to ruthenium tetraoxide is, therefore, both important due to its toxicity and difficult due to the low exposure levels at which the toxicity becomes an issue.

For example, many detection systems or procedures for many different gas phase materials rely on chemically sensitive tapes. Stains are produced due to chemical reactions occurring on the tapes in response to chemical exposure and those stains can then be detected. Problems with such tapes may, however, include sensitivity to different chemicals.

With respect to ruthenium tetraoxide, some useful chemically sensitive tapes are also sensitive to other chemicals such as oxidizing agents. As a result, the tapes typically cannot be used to accurately detect exposure to ruthenium oxide. Other tapes may detect ruthenium oxide, but could not be used to accurately detect at desired exposure levels.

SUMMARY OF THE INVENTION

The present invention provides sensors for and methods of detecting the presence of gas phase materials by detecting the formation of films based on the gas phase material. Advantageously, some gas phase materials preferentially deposit on specific surfaces. As a result, selective detection of those gas phase materials can be obtained by detecting films deposited on those detection surfaces.

In one aspect, the present invention provides for detection of gaseous ruthenium oxide (RuO$_4$) which preferentially deposits on a variety of surfaces, e.g., polypropylene. The deposited film includes elemental ruthenium (Ru) and/or ruthenium oxide (RuO$_2$) which exhibit relatively high electrical conductivity. As a result, detection of gaseous ruthenium oxide may be performed by monitoring electrical conductivity across a detection surface. Exposure levels may be determined based on the increases in electrical conductivity.

Advantages of the present invention include reduced sensitivity to environmental contaminants because relatively few environmental contaminants will deposit on any surface in the form of, e.g., an electrically conductive film. In addition, heating the detection surface may further improve sensitivity to environmental contaminants by reducing or eliminating deposition of environmental moisture and most organic materials.

Detection of the selected material or materials in the gaseous phase may serve a variety of purposes including the detection of toxic/hazardous materials to insure proper industrial safety standards; to monitor reaction levels for process control; to determine the integrity of containment systems; etc.

In one aspect, the present invention provides a method of detecting a gas phase material by providing a sensor including first and second electrodes, a detection surface extending between the first electrode and the second electrode, and a detector operatively connected to the first and second electrodes; exposing the detection surface to the gas phase material, wherein an electrically conductive film forms on the detection surface between the first and second electrodes; and detecting a change in conductivity between the first and second electrodes with the detector.

In another aspect, the present invention provides a method of detecting a gas phase material by providing a sensor including first and second electrodes, a detection surface extending between the first electrode to the second electrode, and a detector operatively connected to the first and second electrodes, wherein the detection surface is not electrically conductive; exposing the sensor to the gas phase material, wherein an electrically conductive film forms on the detection surface between the first and second electrodes; and detecting electrical conductivity of the electrically conductive film between the first and second electrodes with the detector.

In another aspect, the present invention provides a method of detecting a gas phase material by providing a sensor including first and second electrodes, a detection surface extending between the first electrode and the second electrode, and a detector operatively connected to the first and second electrodes; heating the detection surface above ambient temperature; exposing the detection surface to the gas phase material, wherein an electrically conductive film forms on the detection surface between the first and second electrodes; and detecting a change in conductivity between the first and second electrodes with the detector.

In another aspect, the present invention provides a sensor for detecting a gas phase material in an environment, the detector including first and second electrodes; a detection surface extending between the first electrode and the second electrode; and a detector operatively connected to the first and second electrodes.

In yet another aspect, the present invention provides a sensor for detecting a gas phase material in an environment, the detector including first and second electrodes; a detection surface extending between the first electrode and the second electrode; a heater capable of providing thermal energy to the detection surface; and a detector operatively connected to the first and second electrodes.

These and other features and advantages of the present invention are described below with respect to illustrative embodiments of the invention.

BRIEF DESCRIPTION OF THE DRAWINGS

The present invention will be better understood from reading the following description of illustrative embodiments with reference to the attached drawings, wherein below.

DETAILED DESCRIPTION OF ILLUSTRATIVE EMBODIMENTS OF THE INVENTION

The present invention provides devices and methods for the monitoring of gas phase material levels by detecting films formed from the gas phase materials on detection surfaces. One example of an industry using gas phase materials is in the production of semiconductor and other micro-scale devices. Processing steps such as wet etching, dry etching, chemical vapor deposition, etc., may often use or produce gas phase materials that may be, e.g., toxic, corrosive, irritants, etc. Detection of the gas phase materials may be desirable for safety, environmental, or process control purposes.

The present invention relies on the tendencies of the gas phase materials to deposit or form films or coatings on detection surfaces. In some instances, the gas phase materials will preferentially deposit on detection surfaces that are manufactured from particular materials or that have a particular structure. By capitalizing on those preferential deposition tendencies, the present invention offers advantages in monitoring for the materials.

As formed on the detector surface as a result of exposure to the gas phase material, the film may consist essentially of the gas phase material, the film may include one or more constituents in the gas phase material, or the film may be formed of the gas phase material or one or more constituents thereof in addition with other materials, in e.g., a matrix, dispersion, etc.

It may be preferred that, as deposited, the gas phase material or materials form an electrically conductive film or coating on a detection surface. By detecting changes in the conductivity between at least two electrodes on the detection surface, the present invention provides the ability to detect the presence of the gas phase materials.

Typically, deposition rate will be dependent on a variety of factors including, but not limited to the concentration of the selected material in the gaseous state, the properties of the detection surface (e.g., materials, temperature, morphology, etc.), and the environment in which the detection surface is located (e.g., temperature, pressure, etc.). Other variables affecting deposition rate may include deposition-enhancing factors, such as laser-assisted deposition, plasma generation, etc. Regardless of the variables in deposition rate, however, it is preferred that the rate of change in conductivity correlate with exposure levels.

Figure 1:
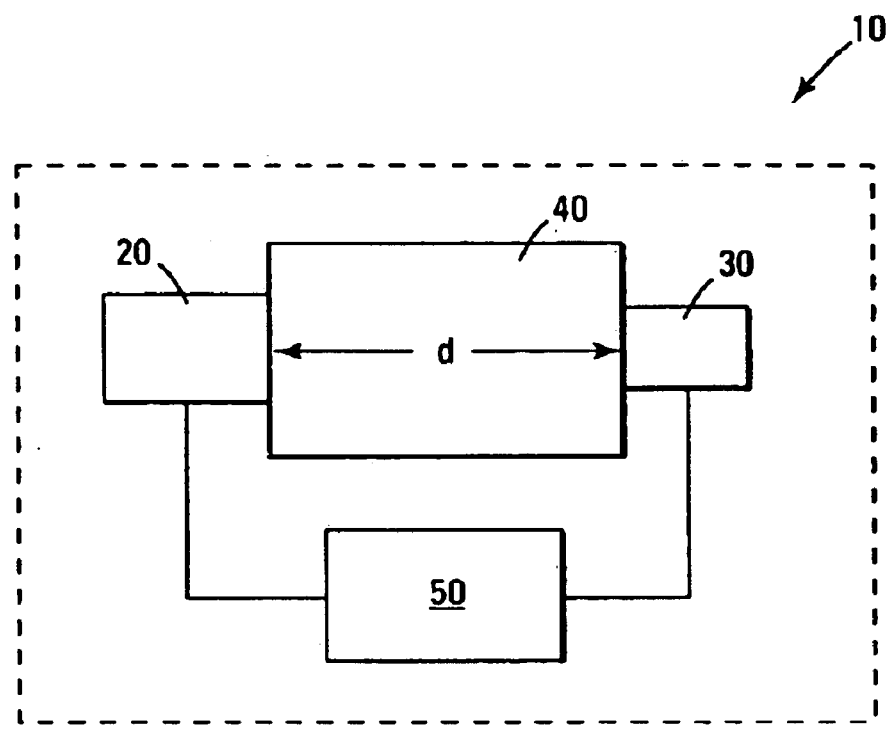
FIG. 1 illustrates one sensor according to the present invention.

FIG. 1 is a schematic diagram of one sensor 10 according to the present invention. The sensor 10 includes a first electrode 20 and second electrode 30. The two electrodes 20 and 30 are separated by a detection surface 40 that extends between the electrodes. The detection surface 40 may preferably electrically isolates the electrodes 20 and 30 such that current is prevented from flowing between the electrodes 20 and 30. Alternatively, the detection surface may provide low level conductivity between the electrodes 20 and 30 that increases as a conductive film is formed thereon.

The electrodes 20 and 30 are each electrically connected to a detector 50 that is capable of detecting a change in conductivity between the electrodes 20 and 30 across the detection surface 40 as a result of deposition of one or more gas phase materials in the form of a film or coating on the detection surface 40. It is preferred that low level depositions of a conductive film on detection surface 40 can produce a finite and accurately measurable change in current flow between electrodes 20 and 30.

The distance d between electrodes 20 and 30 may be used to control the sensitivity of the detector 10 to a particular gas phase material. Factors affecting the selection of an appropriate distance d may include, but are not limited to: resistivity of the deposited film/coating, resistivity of the detection surface 40 before deposition, ambient conditions (humidity, temperature, etc.), temperature of the detection surface 40, size of the electrodes 20 and 30, voltage across the electrodes 20 and 30, etc.

Depending on the properties of the selected material and/or their deposition states, the nature of the detection surface 40 may enhance or retard deposition and either of those results may be desired based on a wide variety of factors. In some instances, the material or materials exposed on the detection surface 40 can affect deposition of the gas phase material. In one illustrative example, gaseous ruthenium oxide preferentially deposits on polypropylene and, as a result, it may be preferred that the detection surface include at least some polypropylene if ruthenium oxide is to be detected.

Alternatively, deposition on the detection surface 40 may be affected by surface morphology, e.g., whether the detection surface 40 is relatively smooth or rough. A rough surface may be structured by, e.g., molding, or randomly roughened by e.g., sandblasting, chemical etching, etc.

Figure 2:
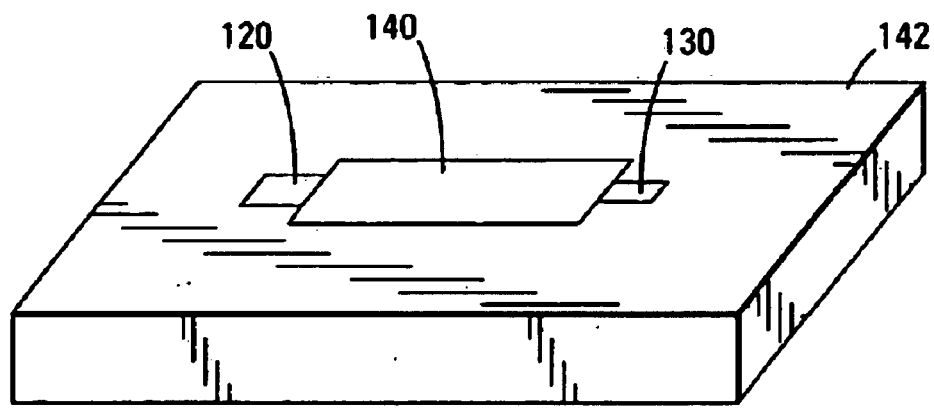
FIG. 2 illustrates another sensor according to the present invention.
Figure 3:
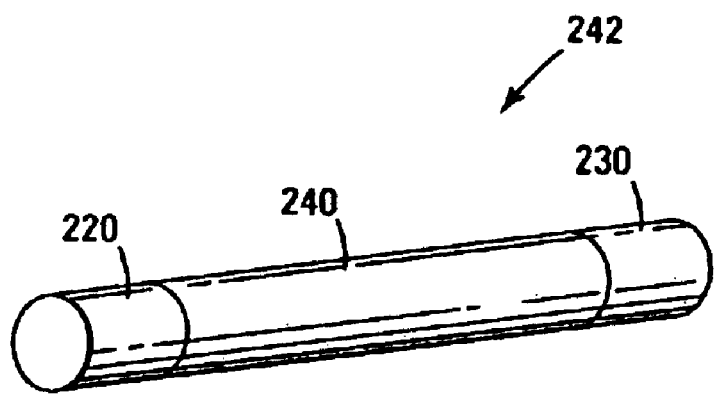
FIG. 3 illustrates another sensor according to the present invention.
Figure 4:
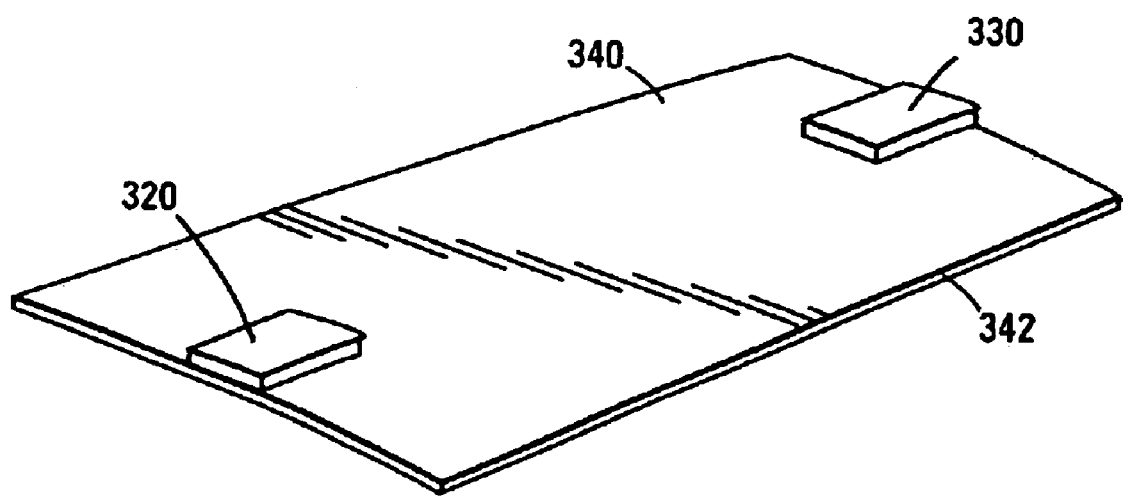
FIG. 4 illustrates another sensor according to the present invention.

Furthermore, the detection surface 40 may be provided in a variety of forms or shapes. Examples of some detection surfaces are depicted in FIGS. 2–4. The detection surface 140 of FIG. 2 is a generally planar surface on a substrate 142 that includes electrodes 120 and 130.

The detection surface 240 of FIG. 3 is provided in the form of a wire 242 with a circular cross-sectional profile, although any desired cross-sectional profile could be used (e.g., square, rectangular, oval, etc.). The electrodes 220 and 230 are preferably located at opposite ends of a portion of the wire 242 and are separated by the detection surface 240.

Although the depicted detection surface 240 extends about the periphery of the wire or rod 242, the detection surface may alternatively be provided as one or more portions of the surface of the wire 242.

FIG. 4 illustrates yet another detection surface 340 provided on a sheet/film 342. Also seen in FIG. 3 are electrodes 320 and 330 separated by the detection surface 340. All or portions of the sheet/film 342 may be treated to enhance or retard deposition of the selected materials as desired to achieve the desired detection sensitivity.

One illustrative method of detecting a selected material in the deposition state will now be described with respect to ruthenium oxide, although it should be understood that the methods of the present invention may be used to detect a variety of other selected materials. Other gas phase materials that could be detected by the device and methods of the present invention include any gas phase material that deposits on a detection surface in the form of an electrically conductive film or coating. It will be understood that the composition of the gas phase material will typically correspond to the composition of the film or coating, but that the exact compositions may be different. For example, gas phase ruthenium tetraoxide ($RuO_4$) can be detected based on a film or coating including elemental ruthenium (Ru) and/or ruthenium dioxide ($RuO_2$), both of which are electrically conductive. Examples of other gas phase materials that can be detected according to the principles of the present invention include, but are not limited to, $IrO_4$ and $RhO_4$.

Ruthenium tetraoxide can be deposited by chemical vapor deposition (CVD) which is defined as the formation of a nonvolatile solid film on a substrate by reaction of vapor phase reactants, i.e., reacting gases, that contain desired components.

In a CVD process, the reacting gases are introduced into the reaction chamber. The gas is decomposed and reacted at a heated wafer surface to form the desired layer. Chemical vapor deposition is just one process of providing thin layers on substrate assemblies and other surfaces, such as films of elemental metals or compounds, e.g., platinum, ruthenium, ruthenium oxide, etc. The CVD process may be enhanced by various related techniques such as plasma assistance, photo assistance, laser assistance, as well as other techniques.

The CVD process for depositing ruthenium and/or ruthenium oxide is conducted with a ruthenium containing precursor being delivered to a reaction chamber. Diluent gases may also optionally be provided to the reaction chamber. One skilled in the art will recognize that the manner in which the gases are introduced into the reaction chamber may include one of various techniques.

Gas products contained within the CVD system are potentially harmful to personnel located around the equipment. The present invention provides methods of detecting the escape of the selected materials based on their deposition onto a detection surface and the resulting change in the conductivity of the detection surface.

Figure 5:
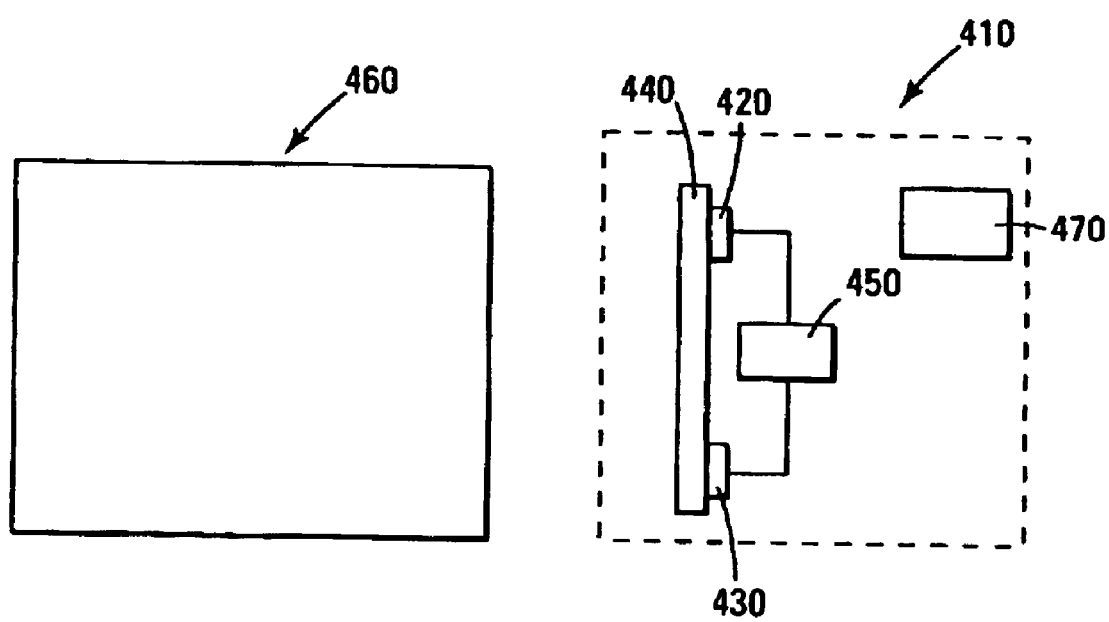
FIG. 5 illustrates one method of using a sensor according to the present invention.

Referring to FIG. 5, a sensor 410 according to the present invention is located in proximity to a CVD system 460 in which ruthenium or ruthenium or ruthenium oxide is to be deposited. In some systems, ruthenium oxide may be formed in the CVD system 460 if it is supplied with oxygen in addition to ruthenium for the purpose of forming ruthenium oxide on a substrate.

A sensor 410 according to the present invention, however, may be able to detect gaseous ruthenium oxide that escapes from the system 460. The sensor 410 includes at least two electrodes 420 and 430, a detection surface 440 extending between the electrodes 420 and 430, and a detector 450 capable of detecting a change in the conductivity between the electrodes 420 and 430. The detector 450 preferably includes an electrical circuit capable of detecting the conductivity change between electrodes 420 and 430 through the film formed on the detection surface 440.

If gas phase ruthenium tetraoxide escapes from the CVD system 460, it will typically form ruthenium oxide by oxidation reduction upon contact with the detection surface 440 of the sensor 410. In the case of ruthenium oxide, the detection surface 440 may include exposed polymeric materials or glass. One example of a useful polymer on which ruthenium oxide may be preferentially deposited is polypropylene, thereby potentially enhancing detection of any gas phase ruthenium oxide. The deposited film or coating is electrically conductive and, as a result, a change in the conductivity of the detection surface 440 between the electrodes 420 and 430 can be used to indicate the presence of ruthenium oxide gas in the area of the sensor 410, thereby alerting personnel in the area or those monitoring an unoccupied area of a potential hazard.

It may be desirable to, e.g., heat the detection surface 440 above the ambient temperature using a heater 470 to potentially enhance sensitivity of the sensor 410. For example, heating the detection surface 440 may limit deposition of ambient moisture vapor or organic materials present in the atmosphere around the detection surface 440. In the case of ruthenium oxide detection, heating the detection surface up to about 100° C. may be useful to enhance detection.

The heater 470 should be capable of providing thermal energy to the detection surface 440 by any suitable manner including conduction, convection, and/or radiation. In addition, the heater 470 may be an electrical resistance heater, operate using RF excitation, infrared radiation, etc.

All patents and references cited herein are incorporated in their entirety as if each were incorporated separately. This invention has been described with reference to illustrative embodiments and is not meant to be construed in a limiting sense. Various modifications of the illustrative embodiments, as well as additional embodiments of the invention, will be apparent to persons skilled in the art upon reference to this description. It is therefore contemplated that the appended claims will cover any such modifications or embodiments that may fall within the scope of the present invention as defined by the accompanying claims.

What is claimed is:

1. A method of detecting a gas phase material comprising:
   locating a sensor outside of a reaction chamber, the sensor comprising:
      a first electrode and a second electrode;
      detection surface extending between the first electrode and the second electrode; and
      a detector operatively connected to the first electrode and the second electrode;
   exposing the detection surface to a gas phase material escaping from the reaction chamber, wherein the gas phase material forms an electrically conductive film on the detection surface;
   detecting the gas phase material from a change in conductivity between the first electrode and the second electrode with the detector; and
   generating an alert based on the detection of the gas phase material.

2. The method according to claim 1, wherein the gas phase material comprises ruthenium.

3. The method according to claim 2, wherein the gas phase material comprises ruthenium tetraoxide.

4. The method according to claim 1, wherein the detection surface is selected such that the electrically conductive film preferentially deposits on the detection surface.

5. The method according to claim 4, wherein selection of the detection surface comprises selecting a detection surface comprising polypropylene.

6. The method according to claim 1, wherein generating the alert comprises alerting personnel in an area surrounding the chamber of a potential hazard.

7. A method of detecting a gas phase material comprising:
providing a sensor outside of, but in proximity to, a reaction chamber, the sensor comprising a first electrode and a second electrode, a detection surface extending between the first electrode and the second electrode, and a detector operatively connected to the first electrode and the second electrode, wherein the detection surface is not electrically conductive;
exposing the sensor to a gas phase material comprising ruthenium escaping from the chamber, wherein an electrically conductive film comprising ruthenium forms on the detection surface;
detecting electrical conductivity of the electrically conductive film between the first and second electrodes with the detector; and
generating an alert based on the detection of the electrical conductivity of the electrically conductive film.

8. The method according to claim 7, wherein the detection surface is selected such that the electrically conductive film comprising ruthenium preferentially deposits on the detection surface.

9. The method according to claim 7, wherein the detection surface comprises a polymer.

10. The method according to claim 7, wherein the detection surface comprises polypropylene.

11. The method according to claim 7, wherein the detection surface comprises glass.

12. A method of detecting a gas phase material comprising:
providing a sensor proximate a reaction chamber, the sensor comprising a first electrode and a second electrode, a detection surface extending between the first electrode and the second electrode, and a detector operatively connected to the first electrode and the second electrode;
heating the detection surface above ambient temperature;
exposing the detection surface to a gas phase material comprising ruthenium escaping from the chamber, wherein an electrically conductive film comprising ruthenium forms on the detection surface;
detecting the electrically conductive film comprising ruthenium from a change in conductivity between the first and second electrodes with the detector; and
generating an alert based on the detection of the electrically conductive film comprising ruthenium.

13. The method according to claim 12, wherein the detection surface is selected such that the electrically conductive film comprising ruthenium preferentially deposits on the detection surface.

14. The method according to claim 13, wherein selection of the detection surface comprises selecting a detection surface comprising polypropylene.

15. The method according to claim 12, wherein heating the detection surface comprises heating the detection surface up to about 100° C. or less.

16. A deposition system comprising:
a reaction chamber for use in semiconductor processing; and
a sensor located outside of the reaction chamber, the sensor operable to detect a gas phase material that escapes from the chamber, the sensor comprising:
a first electrode and a second electrode;
a detection surface extending between the first electrode and the second electrode, wherein the detection surface comprises a material on which an electrically conductive film preferentially deposits from the gas phase material; and
a detector measuring electrical conductivity between the first and second electrodes, where the detector generates an alert when the electrically conductive film forms on the detection surface between the first and second electrodes.

17. The system according to claim 16, wherein the gas phase material comprises ruthenium.

18. The system according to claim 16, wherein the detection surface comprises a polymer.

19. The system according to claim 16, wherein the detection surface comprises polypropylene.

20. The system according to claim 16, wherein the detection surface comprises glass.

21. The system according to claim 16, wherein the detector comprises an electronic circuit capable of detecting a change in electrical conductivity between the first and second electrodes.

22. A deposition system comprising:
reaction chamber for use in depositing film layer by chemical vapor deposition; and
a senor located outside of the chamber and operable to detect a gas phase material comprising ruthenium escaping from the chamber, the sensor comprising:
a first electrode and a second electrode;
a detection surface extending between the first electrode and the second electrode, wherein the detection surface comprises a material on which an electrically conductive film comprising ruthenium preferentially deposits from the gas phase material comprising ruthenium;
a heating apparatus capable of providing thermal energy to detection surface; and
a detector measuring electrical conductivity between the first and second electrodes, where the detector generates an alert when the electrically conductive film comprising ruthenium forms on the detection surface.

23. The system according to claim 22, wherein the detection surface comprises a polymer.

24. The system according to claim 22, wherein the detection surface comprises glass.

* * * * *

UNITED STATES PATENT AND TRADEMARK OFFICE
CERTIFICATE OF CORRECTION

PATENT NO. : 6,897,070 B2
DATED : May 24, 2005
INVENTOR(S) : Guy T. Blalock

It is certified that error appears in the above-identified patent and that said Letters Patent is hereby corrected as shown below:

Column 8,
Line 38, delete "senor" and insert -- sensor --.

Signed and Sealed this

Twenty-fourth Day of January, 2006

JON W. DUDAS
*Director of the United States Patent and Trademark Office*